United States Patent [19]

Snowden

[11] Patent Number: 4,607,109

[45] Date of Patent: Aug. 19, 1986

[54] NITROGEN CONTAINING COMPOUNDS, THEIR PREPARATION AND USE OF SAME FOR THE PREPARATION OF DECALIN KETON DERIVATIVES

[75] Inventor: Roger L. Snowden, Grand-Lancy, Switzerland

[73] Assignee: Firmenich SA, Genvea, Switzerland

[21] Appl. No.: 774,409

[22] Filed: Sep. 10, 1985

[30] Foreign Application Priority Data

Sep. 12, 1984 [CH] Switzerland ..................... 4354/84

[51] Int. Cl.[4] .......................................... C07D 295/00
[52] U.S. Cl. ........................ 548/400; 252/522 R; 568/374
[58] Field of Search .............. 252/522 R; 560/256; 548/400; 568/374

[56] References Cited

U.S. PATENT DOCUMENTS 3,259,646 7/1966 Harris et al. ..................... 568/28
3,988,373 10/1976 Nakamishi et al. .............. 548/400

FOREIGN PATENT DOCUMENTS 1593814 7/1970 France ............................ 252/522
1209398 10/1970 United Kingdom ............. 252/522

OTHER PUBLICATIONS

Snowden, Chemical Abstracts, vol. 101, p. 230790 (1984).

Primary Examiner—Werren B. Lone
Attorney, Agent, or Firm—Pennie & Edmonds

[57] ABSTRACT

Nitrogen containing compounds of formula

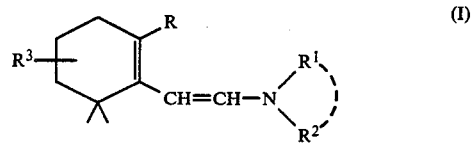

wherein symbol R designates a $C_1$–$C_3$ alkyl group, each of $R^1$ and $R^2$ represents, when taken separately, a $C_1$–$C_6$ alkyl radical or, when taken together, a polymethylene and $R^3$ represents a $C_1$–$C_3$ alkyl group, preferably a methyl radical, or a hydrogen atom.

Process for their preparation comprising the addition of an amine of formula

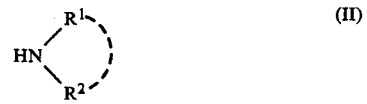

to an aldehyde of formula

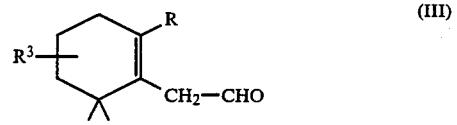

Use of said compounds (I) as starting materials for the preparation of decalin ketone derivatives of general formula

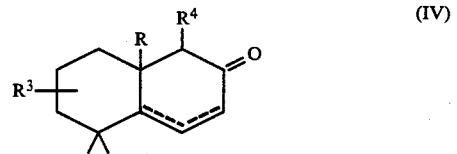

containing a double bond in one of the positions indicated by the dotted lines and wherein $R^4$ designates a hydrogen atom or a methyl radical, and symbols R and $R^3$ have the meaning indicated for formula (I).

4 Claims, No Drawings

NITROGEN CONTAINING COMPOUNDS, THEIR PREPARATION AND USE OF SAME FOR THE PREPARATION OF DECALIN KETON DERIVATIVES

BRIEF SUMMARY OF THE INVENTION

The present invention provides novel nitrogen containing compounds of general formula

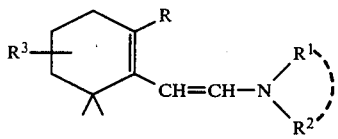

(I)

wherein symbol R designates a $C_1$–$C_3$ alkyl group, each of $R^1$ and $R^2$ represents, when taken separately, a $C_1$–$C_6$ alkyl radical or, when taken together, a polymethylene and $R^3$ represents a $C_1$–$C_3$ alkyl group, preferably a methyl radical, or a hydrogen atom.

The present invention provides also a process for the preparation of said compounds (I), which process is characterized by the addition of an amine of formula

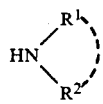

(II)

to an aldehyde of formula

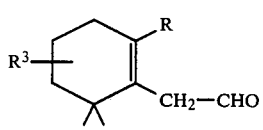

(III)

wherein symbols R, $R^1$, $R^2$ and $R^3$ have the meaning indicated above.

The present invention provides also a utilization of said compounds (I) as starting materials for the preparation of decalin ketone derivatives of general formula

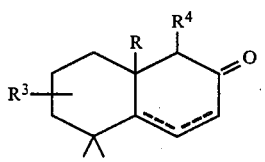

(IV)

containing a double bond in one of the positions indicated by the dotted lines and wherein $R^4$ designates a hydrogen atom or a methyl radical, and symbols R and $R^3$ have the meaning indicated for formula (I). Compounds (I) are converted into decalin ketons(IV) by a process consisting in the following subsequent steps:

a. the addition of compounds (I) to an olefin of formula

(V)

wherein each of symbols $R^4$ and $R^5$ represents a hydrogen atom or a methyl radical and Z designates a —CN radical or a $C(O)OR^6$, wherein $R^6$ stands for an alkyl radical, preferably a $C_1$–$C_4$ alkyl, or an araliphatic radical;

b. the treatment of the resulting compound with acetic anhydride or, alternatively, the thermal treatment of it to give a compound of formula

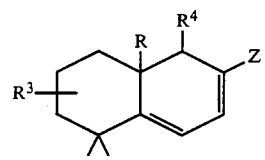

(VI)

c. the treatment of compound (VI) with an alkali metal hydroxyde to give an acid of formula

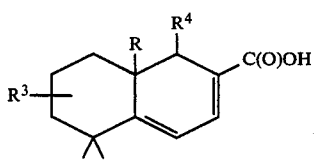

(VII)

d. the conversion of acid (VII) into desired ketone (IV) by a degradation reaction.

The instant invention provides further decalin ketones of formula

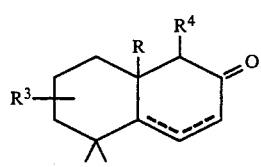

(IV)

containing a double bond in one of the positions indicated by the dotted lines and wherein R designates a $C_1$–$C_3$ alkyl group, $R^3$ represents a $C_1$–$C_3$ alkyl radical, preferably methyl or a hydrogen atom, and $R^4$ stands for a hydrogen atom or a methyl radical.

The instant invention relates also to decalin esters of formula

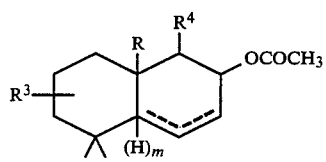

(VIIIa′)

having an optional double bond in one of the positions indicated by the dotted lines and wherein m stands for zero or one, R designates a $C_1$–$C_3$ alkyl radical, $R^3$ represents a $C_1$–$C_3$ alkyl, preferably methyl, or a hydrogen atom and $R^4$ designates a hydrogen atom or a methyl radical, with the proviso that R cannot be methyl and R hydrogen simultaneously when $R^4$=H and the formula does not possess double bonds in the position indicated by the dotted lines.

The instant invention relates further to the utilization of said esters of formula (VIIIa′) as active perfume ingredients.

THE INVENTION

The novel nitrogen containing compounds (I) of this invention are useful starting materials for the preparation of decalin ketone derivatives (IV) which represent advantageous intermediates in the synthesis of valuable perfume ingredients (see Swiss Pat. No. 536,804).

As indicated above, symbols R and $R^3$ designate $C_1$–$C_3$ alkyl radicals. Typically, they stand for a methyl, an ethyl, a n-propyl or an isopropyl radical. Preferably, R represents a methyl or an ethyl group, whereas $R^3$ is preferably a methyl.

Substituents $R^1$ and $R^3$ can represent, taken separately, methyl, ethyl, n-propyl, isopropyl, n-butyl, sec-butyl, tert-butyl, pentyl or hexyl, or, taken together, a polymethylene. Preferably, they stand for a methyl or a tetramethylene radical; in this latter case, they define, together with the nitrogen atom to which they are bound, a pyrrolidinyl group.

Substituent $R^3$ can be bound to the cyclohexenic ring to anyone of the allowable positions. Thus, formula (I) designates, for example, one of the following preferred compounds:

[2-(2,6,6-trimethyl-1-cyclohexen-1-yl)-1-ethenyl]-pyrrolidine,
[2-(2-ethyl-6,6-dimethyl-1-cyclohexen-1-yl)-1-ethenyl]-pyrrolidine,
N,N-dimethyl-[2-(2,6,6-trimethyl-1-cyclohexen-1-yl)-1-ethenyl]-amine,
N,N-dimethyl-[2-(2-ethyl-6,6-dimethyl-1-cyclohexen-1-yl)-1-ethenyl]-amine,
[2-(2,3,6,6-tetramethyl-1-cyclohexen-1-yl)-1-ethenyl]-pyrrolidine,
[2-(2-ethyl-3,6,6-trimethyl-1-cyclohexen-1-yl)-1-ethenyl]-pyrrolidine,
[2-(2-ethyl-4,6,6-trimethyl-1-cyclohexen-1-yl)-1-ethenyl]-pyrrolidine,
[2-(2-ethyl-5,6,6-trimethyl-1-cyclohexen-1-yl)-1-ethenyl]-pyrrolidine,
[2-(2,4,6,6-tetramethyl-1-cyclohexen-1-yl)-1-ethenyl]-pyrrolidine,
[2-(2,5,6,6-tetramethyl-1-cyclohexen-1-yl)-1-ethenyl]-pyrrolidine,
N,N-dimethyl-[2-(2,3,6,6-tetramethyl-1-cyclohexen-1-yl)-1-ethenyl]-amine,
N,N-dimethyl-[2-(2,4,6,6-tetramethyl-1-cyclohexen-1-yl)-1-ethenyl]-amine,
N,N-dimethyl-[2-(2,5,6,6-tetramethyl-1-cyclohexen-1-yl)-1-ethenyl]-amine,
N,N-dimethyl-[2-(2-ethyl-3,6,6-trimethyl-1-cyclohexen-1-yl)-1-ethenyl]-amine,
N,N-dimethyl-[2-(2-ethyl-4,6,6-trimethyl-1-cyclohexen-1-yl)-1-ethenyl]-amine,
N,N-dimethyl-[2-(2-ethyl-5,6,6-trimethyl-1-cyclohexen-1-yl)-1-ethenyl]-amine.

As indicated above, compounds (I) are converted into ketones (IV) according to an original multistep process wherein however each of the discreet steps are conventional in the art.

The last step is carried out e.g. by treating acid (VII) with thionyl chloride, reacting the obtained acyl chloride with sodium azide, subjecting the formed azide to a thermal treatment and heating the resulting isocyanate in acidic medium. This process is known in the art as a Curtius type degradation reaction and is described in a detailed manner in the examples which follow. Other known methods can also be employed successfully. Step b can be effected according to two distinct routes.

One comprises the step of treating the product resulting from step. a with acetic anhydride; the other consists in subjecting said product to a thermal treatment, for example to a temperature higher than 150° C., preferably at about 150°–200° C. Ketones (IV) are novel chemical entities.

Their conversion into decalin esters (VIIIa)

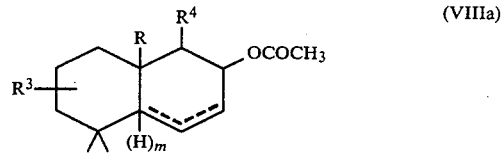

having a double bond in one of the positions indicated by the dotted lines, and wherein substituents R, $R^3$ and $R^4$ have the meaning indicated above and index m stands for zero or one, can be carried out by reduction of the ketonic function by means of a current reduction reagent such as sodium borohydride or diisobutyl aluminoahydride, followed by esterification of the obtained carbinol.

Esters (VIIIa) can occur under different isomeric form; their predominant one however is the trans decalinic (about 80%) defined by general formula

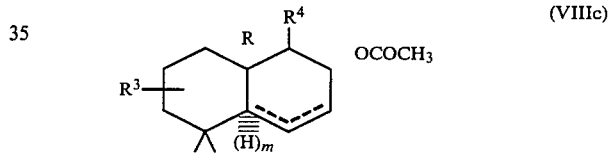

By effecting the reduction of said ketones by catalytic hydrogenation, for instance under pressure and in the presence of Raney nickel, there will be obtained isomeric mixtures of decalin esters of formula

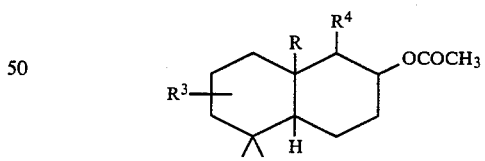

whose main constituent is the trans decalin isomer of formula

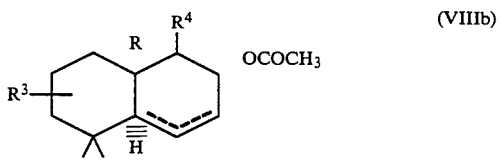

Certain among the obtained esters are new. These are defined by general formula

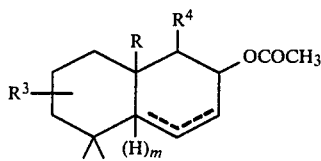

(VIIIa')

Formula (VIIIa') include the following compounds:

1,2,3,5,6,7,8,8a-octahydro-4,4,8aβ-trimethyl-2β-naphthyl acetate, 1,2,4a,5,6,7,8,8a-octahydro-5,5,8aβ-trimethyl-2βtrans-naphthyl acetate, 8aβ-ethyl-perhydro-5,5-dimethyl-2β-trans-naphthyl acetate and perhydro-5,5,6,8aβ-tetramethyl-2βtrans-naphthyl acetate.

New esters of formula (VIIIa'), much to the same extent as the known compounds of the art, viz. described in Swiss Pat. No. 536,804, are compounds possessing very advantageous odorous properties and consequently can be used as perfume ingredients in the preparation of perfumes and perfumed products. They develop very elegant woody notes and find a utilization in a variety of perfume compositions of different nature.

The invention is illustrated in a more detailed manner by the following examples wherein the temperature are indicated in degrees centigrade and the abbreviations have the meaning common in the art. NMR spectra are recorded by dissolving the sample under examination in deuterochloroform.

EXAMPLE 1

1,2,3,5,6,7,8,8a-octahydro-5,5,8aβ-trimethyl-2β-naphthyl acetate 0.36 G (1.86 mM) of 1,2,3,5,6,7,8,8a-octahydro-5-5-8aβ-trimethyl-2β-naphthol were mixed with 0.32 g (3.2 mM) of acetic anhydride and 10 ml of pyridine and the mixture was kept at reflux for 5 h 30. The usual treatments of extraction and separation allowed the isolation of a colorless oil (0.42 g; yield: 96%) constituted by the desired product having bp 180°–200° (bath temperature)/13.3 Pa. $R_F$(cyclohexane/ethyl acetate 8:2): 0.53

IR: 1730, 1460, 1374, 1360, 1250, 1230, 1210, 1030, 960, 866, 820, 660, 600 cm$^{-1}$;

NMR: 1.07; 1.13; 1.25 (3s, 9H); 1.0–2.5 (10H), 2.02 (s, 3H); 5.03 (m, 1H); 5.37 (m, 1H) δppm;

MS: M$^+$=236; m/e: 176(58), 161(42), 133(18), 119(39), 105(94), 91(100).

By following the same procedure as that indicated above, there is obtained the corresponding diastereoisiomer starting from 1,2,3,5,6,7,8,8a-octahydro-5,5,8aβ-trimethyl-2α-naphthol.

IR (CDCl$_3$): 1725, 1460, 1368, 1260, 1030, 650 cm$^{-1}$;

NMR: 1.07 (s, 6H); 1.27 (s, 3H); 1.0–2.5 (10H); 2.03 (s, 3H); 5.05 (m, 1H); 5.30 (m, 1H) δppm;

SM: M$^+$=236; m/e: 176(50), 161(41), 133(18), 119(35), 105(95), 91(100).

The starting naphthol was prepared as follows:

a. (2,6,6-trimethyl-1-cyclohexen-1-yl)-acetaldehyde

A solution of 100 g of 1-ethynyl-2,6,6-trimethyl-1-cyclohexanol (0.6M) (see Swiss Pat. No. 636,009) in 500 ml of xylene and 5 g of silylvanadate, obtained as indicated hereinafter, was kept at reflux for 23 h. After evaporation of the solvent, there was obtained by fractional distillation of the residue the desired aldehyde under the form of a colorless oil (77 g; yield: 77%); bp 109°–110°/2×10$^3$ Pa.

Silylvanadate: A solution of diphenylsilyl dichloride (45.0 g; 0.16M) in 130 ml of acetone was added dropwise at 25° during 20 mm to a solution of sodium orthovanadate (Na$_3$VO$_4$)(10.0 g; 0.05M) in 150 ml of water. The temperature of the reaction mixture rose gradually up to 35°–40° while the stirring was kept for 10 mn. The mixture was then cooled in an ice bath and 350 ml of ice water were added thereto, the mixture was stirring during 5 mn, and then filtered. The solid collected was washed twice with water and dried at 66.5 Pa over anhydrous CaCl$_2$. Yield: 35.1 g.

b. N,N-dimethyl-[2-(2,6,6-trimethyl-1-cyclohexen-1-yl)-1-ethenyl]-amine

A mixture of 5 g of (0.03M), 25 ml of toluene and 3.7 g (0.033M) of a 40% aqueous solution of dimethylamine was stirred at 60° during 1 h. The organic phase was separated, washed with water and with a concentrated aqueous solution of NaCl and dried over anhydrous Na$_2$SO$_4$. After evaporation of the solvent and fractional distillation of the residue, 5.63 g (yield: 97%) of the desired amine were obtained; bp 120° (bath temperature)/1.33 Pa.

IR: 1640, 1450, 1350, 1140, 1080, 940, 780 and 718 cm$^{-1}$;

NMR: 0.99 (6H); 1.3–2.2 (9H); 2.61 (s, 6H); 4.58 (large d, J=14 Hz, 1H); 5.82 (d, J=14 Hz, 1H) δppm;

MS: M$^+$=193(100); m/e: 178(71), 133(17), 122(29), 108(26).

The reaction proceeds in an analogous way by using xylene instead of toluene.

c. methyl 5,5,8a-trimethyl-1,5,6,7,8,8a-hexahydro-naphthalene-carboxylate

A solution of 3.86 g (20 mM) of the amine obtained according to letter b above, 3.44 g (40 mM) of methyl acrylate in 20 ml of toluene containing 20 mg of hydroquinine was heated in an autoclave of stainless steel under nitrogen at 150° during 3 h. Then, 4.1 g (40 mM) of acetic anhydride were added and the mixture was heated at 150° during 1 h. The evaporation of the solvent and distillation of the residue gave 3.95 g (yield: 84%) of the desired ester; bp 160°–180°/2.66 Pa.

IR: 1710, 1570, 1460, 1440, 1260, 1225, 1100, 850, 740 and 670 cm$^{-1}$;

NMR: 1.03 (s, 3H); 1.16 (6H); 1.2–2.0 (6H); 2.31 (2H, ABqa, J=16 Hz); 3.76 (s, 3H); 6.0 (d, J=6 Hz, 1H); 7.0 (d×d, J=6 and 2.5 Hz, 1H) δppm;

MS: M$^+$=234(50); m/e: 219(31), 164(100), 149(67), 119(50), 105(86), 91(54).

d. 5,5,8a-trimethyl-1,5,6,7,8,8a-hexahydro-naphthalene-carboxylic acid

A solution of 2.34 g (10 mM) of the ester obtained under letter c. above in 5 ml of methanol was added dropwise to a stirred solution of KOH (1.7 g; 30 mM) in 15 ml of methanol at 25°. The mixture was kept at reflux for 5 h. Then, after evaporation of methanol, water was added thereto. After acidification with aqueous HCl, extraction with ethyl acetate followed by the usual treatments of the organic extracts, 2.06 g (yield 94%) of the desired acid was obtained under the form of a crystallin solid, F. 184°–185.5°.

IR (CDCl$_3$): 3050, 1670, 1630, 1560, 1420, 1280, 1230, 854, 820 cm$^{-1}$;

NMR: 1.03 (s, 3H); 1.16 (6H); 1.2–2.0 (6H); 2.20 (ABqa, J=16 Hz, 2H); 6.05 (d, J=6 Hz, 1H); 7.16 (d×d, J=6 and 2.5 Hz, 1H); 11.25 (large s, 1H) δppm;

MS: M+ =220(35); m/e: 205(18), 150(100), 135(60), 119(30), 105(75), 91(88).

Analogous results were observed by replacing methyl acrylate by n-butyl and benzyl acrylate.

e. 1,2,4a,5,6,7,8,8a-octahydro-5,5,8acis-trimethyl-naphthalen-2-one, 1,2,3,5,6,7,8,8a-octahydro-5,5,8a-trimethyl-naphthalen-2-one and 1,2,4a,5,6,7,8,8a-octahydro-5,5,8atrans-trimethyl-naphthalen-2-one A mixture of 11 g (0.05M) of the acid obtained under letter d. above and 8.9 g (0.075M) of SOCl₂ was refluxed for 3 h. After evaporation of the excess of SOCl₂ under reduced pressure (2×10³ Pa), the residue was distilled at 26.6 Pa to give the desired acyl chloride under the form of a pale yellow oil (11.3 g; bp 120°-122°/26.6 Pa).

A solution of the acyl chloride in 30 ml of acetone was added dropwise during 20 mn to a stirred solution of sodium azide (4.3 g; 66 mM) in 20 ml of water at 0°-5°. The temperature of the mixture was then raised to 25° in 1 h and kept at this value for 2 further hours. The extraction with 3 fractions of 30 ml each of toluene and the usual treatments of the extracts allowed to obtain the acyl azide in toluene solution (40-50 ml). After azeotropic drying, the solution was added dropwise in 20 mn to 60 ml of toluene kept under stirring at 100°-110° to give the corresponding isocyanate. To the thus obtained solution kept at 100°, 5 ml of aqueous HCl were added dropwise during 5 mn.

The reaction was accompanied by a rapid liberation of CO₂ which ended after approximately 75-80 mn. The reaction mixture was then neutralized with a saturated aqueous solution of sodium bicarbonate, extracted, subjected to the usual treatments and distilled (bp 82°-92°/26.6 Pa). The fraction thus obtained was constituted by a mixture of the desired three ketones under the form of a colorless oil (7.1 g; yield: 74%). The isolation of the three pure products was effected by column chromatography (support: SiO₂; eluent: cyclohexane/ethyl acetate).

1,2,3,5,6,7,8,8a-octahydro-5,5,8a-trimethyl-naphthalen-2-one

IR: 1725, 1460, 1380, 1320, 1265, 1230, 990, 850, 670 cm⁻¹;
NMR: 1.10 (6H); 1.16 (3H); 1.0-2.0 (6H); 2.30 (ABqa, J=13 Hz, 2H); 2.87 (m, 2H); 5.57 (t, J=4 Hz, 2H) δppm;
MS: M+ =192(37); m/e: 177(17), 150(30), 135(100), 122(14), 107(29), 93(31), 79(25).

1,2,4a,5,6,7,8,8a-octahydro-5,5,8acis-trimethyl-naphthalen-2-one

NMR (¹H): 0.88; 1.00; 1.07 (3s, 9H); 1.2-1.6 (6H); 2.3 (ABqa; J=18 Hz, 2H); 6.11 (d, J=10 Hz, 1H); 6.98 (d×d, J=10 and 6 Hz, 1H) δppm;
NMR (¹³C): 200.6s; 150.6d; 129.6d; 53.0d; 46.4t; 41.3t; 40.2t; 35.0s; 32.8qa; 31.7qa; 23.1qa; 18.8t Δppm;
MS: M+ =192(8); m/e: 177(4), 149(19), 121(13), 109(100), 91(9), 79(18).

1,2,4a,5,6,7,8,8a-octahydro-5,5,8-atrans-trimethyl-naphthalen-2-one

IR: 1680, 1460, 1380, 1250, 1170, 880, 820, 720 cm⁻¹;
NMR (¹H): 0.91, 1.00 and 1.03 (3s, 9H); 1.2-1.8 (6H); 2.21 (m, 2H); 6.07 (d×d, J=10 and 3 Hz, 1H); 6.98 (d×d, J=10 and 2 Hz, 1H) δppm;
NMR (¹³C): 199.7s; 150.5d; 130.2d; 58.0t; 54.6d; 41.5t; 40.4t; 39.8s; 32.5qa; 22.0qa; 18.8qa; 18.5t Δppm;

MS: M+ =192(25); m/e: 177(7), 149(14), 135(15), 122(70), 109(100), 81(45).

f. 4 G (20.8 mM) of the mixture of the ketones obtained under letter e. above in methanol were hydrogenated in the presence of Raney nickel during 1 day at 8 bars/40°. After filtration, evaporation and distillation [180° (bath temperature)/13.3 Pa], a mixture of the following four carbinols was obtained:

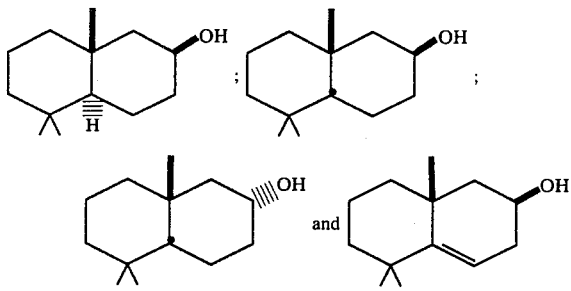

g. 1 G (5.1 mM) of the said mixture and 0.8 g (7.8 mM) of acetic anhydride in 15 ml of pyridine were refluxed for 3 h. After distillation of the excess of pyridine, 10% HCl were added to the mixture and followed by extraction to give the corresponding acetate (1.1 g; yield: 91%).

EXAMPLE 2

1,2,4a,5,6,7,8,8a-octahydro-5,5,8aβtrans-trimethyl-2β-naphthyl and
1,2,4a,5,6,7,8,8a-octahydro-5,5,8aβtrans-trimethyl-2α-naphthyl acetate By following the same procedure as that indicated in the previous example, the title esters were prepared starting from 1,2,4a,5,6,7,8,8a-octahydro-5,5,8atrans-trimethyl-naphthalen-2-one. The obtained esters showed the following analytical characters.

1,2,4a,5,6,7,8,8a-octahydro-5,5,8aβtrans-trimethyl-2β-naphthyl acetate

IR: 1730, 1460, 1370, 1240, 1120, 1030, 960, 910 and 810 cm⁻¹;
NMR: 0.87, 0.93 and 1.00 (3s, 9H); 1.0-2.2 (9H); 2.01 (s, 3H); 5.23 (m, 1H); 5.83 (m, 2H) δppm;
MS: M+ =236; m/e: 194(16), 176(74), 161(52), 133(30), 119(35), 105(85), 91(100).

1,2,4a,5,6,7,8,8a-octahydro-5,5,8aβtrans-trimethyl-2α-naphthyl acetate

IR: 1740, 1460, 1375, 1240, 1024, 982, 950, 924 and 806 cm⁻¹;
NMR: 0.83, 0.93 and 1.01 (3s, 9H); 1.0-2.2 (9H); 2.03 (s, 3H); 5.50 (m, 1H); 5.76 (m, 2H) δppm;
MS: M+ =236; m/e: 194(12), 176(75), 161(52), 133(32), 119(34), 105(91), 91(100).

EXAMPLE 3

Perhydro-5,5,6,8aβ-tetramethyl-2β-trans-naphthyl acetate

2 G (9.7 mM) of a solution constituted by a mixture in methanol of 1,2,3,5,6,7,8,8a-octahydro-5,5,6,8a-tetramethyl-naphthalen-2-one and 1,2,4a,5,6,7,8,8a-octahydro-5,5,6,8a-tetramethyl-naphthalen-2-one (obtained as indicated above) were reduced by catalytic hydrogenation at 80° under 15 bars during 88 h by means of Raney nickel. The obtained mixture of alcohols was acetylated with acetic anhydride in the presence of anhydrous sodium acetate in toluene. The obtained mixture of acetates was subjected to column chromatography (eluent: cyclohexane/ethyl acetate) to give a colorless oil consisting of the desired acetate. Yield: 36%, 880 mg. Bp 200° (bath temperature)/6.65 Pa.

IR: 1730, 1450, 1375, 1360, 1260, 1240, 1160, 1060, 1020 cm$^{-1}$;

NMR: 0.65–2.00 (24H); 2.02 (s, 3H); 5.00 (m, 1H) δppm;

MS: M$^+$ = 252; m/e: 192 (33), 177 (69), 138 (100), 123 (76), 108 (52), 93 (76).

The mixture of naphthalenones used as starting materials in the above preparation were obtained as follows.

a. (2,5,6,6-Tetramethyl-1-cyclohexenyl)-acetaldehyde

A solution of 2,2,3,6-tetramethyl-1-ethynyl-1-cyclohexanol (15 g; 0.083M) in 100 ml of xylene was refluxed during 20 h in the presence of 2 g of diphenylsilyl vanadate. After evaporation of xylene and distillation of the obtained residue, 13 g (yield: 87%) of the desired aldehyde were obtained. Bp 48°–52°/6.65 Pa.

IR: 2730, 1725, 1460, 1390, 1380, 1364, 1070 and 1040 cm$^{-1}$.

b. Methyl 1,5,6,7,8,8a-hexahydro-5,5,6,8a-tetramethyl-naphthalene-carboxylate

A mixture of 13 g (0.072M) of the aldehyde obtained under letter a. above, 15.4 ml (0.12M) of 40% dimethylamine and 70 ml of xylene was stirred at 90° for 3 h. The separation of the different layers was followed by extraction with xylene of the aqueous phase and the usual treatments of washing and drying. After filtration, 13.5 g (0.16M) of methyl acrylate were added to the clear filtrate and the mixture was heated at 180° for 24 h in a stainless steel autoclave. Evaporation of the solvent and distillation of the residue gave 13.2 g (yield: 74%) of a colorless oil; bp 112°–115°/4 Pa.

IR: 1710, 1566, 1440, 1380, 1096, 854, 742 and 680 cm$^{-1}$.

c. 1,5,6,7,8,8a-Hexahydro-5,5,6,8a-tetramethyl-naphthalene-carboxylic acid

A solution of 12.5 g (0.05M) of the ester obtained under letter b above and 6.5 g of KOH (0.12M) in 100 ml of methanol was heated at reflux for 4 h. After evaporation of methanol, water has been added to the residue and the alkaline solution was extracted with ether and the aqueous phase acidified with 10% HCl. The desired raw material was collected by filtration and washing with water and acetone followed by drying over P$_2$O$_5$ vacuum. Yield: 94%; 11 g. Mp 151°–182°.

IR (KBr): 2900, 1670, 1625, 1555, 1420, 1275, 1090, 1040, 845, 745 and 670 cm$^{-1}$;

NMR: 0.85–0.90 (2t, J=7 Hz; 3H); 0.92; 0.95; 1.06, 1.13 and 1.18 (9H); 1.25–1.70 (4H); 2.05 (1H); 2.18 (2ABq, J=16 Hz, 2H); 5.98 and 6.08 (2d, J=6 Hz; 1H); 6.90 (1H) δppm;

MS: M$^+$ = 234; m/e: 220 (19), 163 (29), 150 (100), 135 (46), 119 (39), 105 (82), 91 (79).

d. 5 G (0.021M) of the acid obtained under letter c above were subjected to a Curtius type degradation reaction according to Example 1 (see paragraph e) to give 3.4 g (yield: 77%) of the desired mixture of ketones. A column chromatography (eluent: cyclohexane/ethyl acetate) on a silica support gave 0.63 g of a colorless oil constituted by 1,2,3,5,6,7,8,8a-octahydro-5,5,6,8aβ-tetramethyl-naphthalen-2-one having bp 150° (bath temperature)/6.6 Pa.

IR: 1730, 1680, 1460, 1380, 1240, 1010, 840 and 678 cm$^{-1}$;

NMR: 0.79 (d, J=7 Hz, 3H); 0.97 (s, 3H); 1.10 and 1.20 (2s, 6H); 1.00–2.50 (5H); 2.30 (ABq, J=13 Hz, 2H); 2.87 (t, J=4 Hz, 2H); 5.57 (t, J=4 Hz, 1H) δppm;

MS: M$^+$ = 206; m/e: 191 (23), 164 (24), 149 (100), 122 (47), 107 (57).

EXAMPLE 4

1,2,3,5,6,7,8,8a-Octahydro-5,5,6,8aβ-tetramethyl-naphthyl acetate a. A solution of 1 g (4.85 mM) of 1,2,3,5,6,7,8,8a-octahydro-5,5,6,8aβ-tetramethyl-naphthalen-2-one (see Example 2, paragraph d.) in 5 ml of methanol was added dropwise at 25° under stirring to a suspension of 0.5 g (13.2 mM) of NaBH$_4$ in 100 ml of ethanol. After 3 h, the reaction mixture was acidified with 10% aqueous HCl and extracted with ether. By the usual treatments followed by column chromatography (silica; eluent: cyclohexane/ethyl acetate 8:2), a colorless oil was obtained: 0.860 g (yield: 85%) constituted by 1,2,3,5,6,7,8,8a-octahydro-5,5,6,8aβ-tetramethyl-naphthalen-2-ol. Bp 200° (bath temperature/6.6 Pa).

b. A mixture of 0.750 g (3.6 mM) of the naphthalenol obtained under letter a. above, 0.750 g (7.4 mM) of acetic anhydride and 0.353 g (4.2 mM) of anhydrous sodium acetate in 15 ml of toluene was refluxed for 3 h under nitrogen. The usual treatments allowed to obtain the desired ester as a colorless oil (0.870 g; yield: 97%). Bp 200° (bath temperature)/13.3 Pa.

IR: 1730, 1460, 1380, 1360, 1240, 1220, 1130, 1050 and 1020 cm$^{-1}$;

NMR: 0.82 (d, J=8 Hz, 3H); 1.00 (s, 3H); 1.23 and 1.28 (2s, 6H); 2.02 (s, 3H); 2.33 (m, 2H); 5.06 (m, 1H); 5.36 (m, 1H) δppm;

MS: M$^+$ = 250; m/e: 190 (21), 175 (18), 147 (8), 133 (15), 119 (36), 106 (100), 91 (60).

NMR ($^{13}$C): 170.8 (s); 148.0 (s); 116.9 (d); 68.8 (d); 45.9 (t); 39.9 (d); 39.4 (s); 35.8 (t); 34.6 (s); 31.9 (t) 30.9 (q); 29.4 (q); 29.0 (q); 25.7 (t); 21.5 (q); 15.9 (q) δppm.

EXAMPLE 5

Perhydro-5,5-dimethyl-8aβ-ethyl-2βtrans-naphthyl acetate

This ester was prepared by catalytic reduction in the presence of Raney nickel of 1,2,3,5,6,7,8,8a-octahydro-5,5-dimethyl-8a-ethyl-naphthalen-2-one according to the process described in Example 3. Bp 200° (bath temperature)/13.3 Pa.

IR: 1740, 1460, 1380, 1364, 1260, 1240, 1180, 1160, 1050, 1020, 960 and 740 cm$^{-1}$;

NMR ($^1$H): 0.73 (t, J=7 Hz, 3H); 0.87 and 0.88 (2s, 6H); 0.85–2.10 (15H); 2.02 (s, 3H); 5.02 (m, 1H) δppm;

MS: M$^+$ = 252; m/e: 192 (27), 177 (30), 163 (100), 149 (23), 138 (55), 123 (62), 109 (67), 95 (56), 81 (89).

The starting naphthalenone was prepared according to the procedure described in Example 3 starting from 2,2-dimethyl-6-ethyl-1-ethynyl-1-cyclohexanol.

What I claim is:

1. Nitrogen containing compounds of general formula

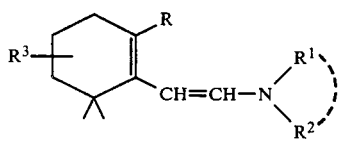 (I)

wherein symbol R designates a $C_1$–$C_3$ alkyl group, each of $R^1$ and $R^2$ represents, when taken separately, a $C_1$–$C_6$ alkyl radical or, when taken together, a polymethylene and $R^3$ represents a $C_1$–$C_3$ alkyl group, preferably a methyl radical, or a hydrogen atom.

2. Compounds according to claim 1 wherein substituent R of formula (I) designates a methyl radical, and $R^1$ and $R^2$, taken together, designate a $-(CH_2)_4-$ radical or each of them, taken separately, stands for a methyl.

3. Compounds according to claim 1 wherein substituent R of formula (I) designates an ethyl radical, and $R^1$ and $R^2$, taken together, designate a $-(CH_2)_4-$ radical or each of them, taken separately, stands for a methyl.

4. Process for the preparation of the compounds according to claim 1 which comprises the addition of an amine of formula

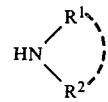 (II)

to an aldehyde of formula

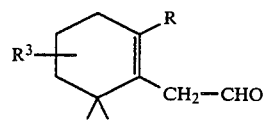 (III)

wherein symbols R, $R^1$, $R^2$ and $R^3$ have the meaning given for formula (I) in claim 1.

* * * * *